United States Patent
Craine et al.

(10) Patent No.: US 6,378,782 B1
(45) Date of Patent: Apr. 30, 2002

(54) METHOD AND APPARATUS FOR APPLYING A CONTROLLED PATTERN OF FIBROUS MATERIAL TO A MOVING SUBSTRATE

(75) Inventors: Andrew W. Craine, Altharetta; Scott Richard Miller, Roswell; Tommy A. Pelletier, Alpharetta; Paul Andrew Schmidt, Sugar Hill, all of GA (US)

(73) Assignee: Nordson Corporation, Westlake, OH (US)

( * ) Notice: Subject to any disclaimer, the term of this patent is extended or adjusted under 35 U.S.C. 154(b) by 0 days.

(21) Appl. No.: 09/429,843

(22) Filed: Oct. 29, 1999

Related U.S. Application Data

(63) Continuation-in-part of application No. PCT/US99/08519, filed on Apr. 16, 1999.
(60) Provisional application No. 60/082,069, filed on Apr. 17, 1998.

(51) Int. Cl.$^7$ .................................................. B05B 1/00
(52) U.S. Cl. ...................... 239/270; 239/294; 239/298
(58) Field of Search ................................ 239/270, 294, 239/298, 290; 118/313

(56) References Cited

U.S. PATENT DOCUMENTS

| | | | |
|---|---|---|---|
| 3,920,362 A | | 11/1975 | Bradt .......................... 425/72 |
| 4,031,854 A | * | 6/1977 | Sprague ...................... 239/406 |
| 4,785,996 A | | 11/1988 | Ziecker et al. ............... 239/298 |
| 4,815,660 A | * | 3/1989 | Boger .......................... 239/11 |
| 4,844,003 A | * | 7/1989 | Statterback et al. ......... 239/270 |
| 4,960,619 A | | 10/1990 | Slautterback et al. ....... 427/265 |
| 4,983,109 A | | 1/1991 | Miller et al. .................... 425/7 |
| 5,207,970 A | | 5/1993 | Joseph et al. ................ 264/518 |
| 5,292,068 A | | 3/1994 | Raterman et al. ............. 239/11 |
| 5,354,378 A | | 10/1994 | Hauser et al. ............... 118/696 |
| 5,421,921 A | | 6/1995 | Gill et al. ................... 156/62.4 |
| 5,431,343 A | | 7/1995 | Kubiak et al. ............... 239/105 |
| 5,458,291 A | | 10/1995 | Brusko et al. ............... 239/423 |
| 5,620,139 A | | 4/1997 | Ziecker ....................... 239/124 |
| 5,679,379 A | | 10/1997 | Fabbricante et al. ........... 425/7 |
| 5,700,322 A | | 12/1997 | Fort ............................. 118/50 |
| 5,882,573 A | | 3/1999 | Kwok et al. ................. 264/510 |
| 5,902,540 A | | 5/1999 | Kwok .......................... 264/555 |
| 5,904,298 A | | 5/1999 | Kwok et al. ................. 239/135 |

FOREIGN PATENT DOCUMENTS

| | | |
|---|---|---|
| DE | 3543469 A1 | 6/1987 |
| JP | 9-164358 | 6/1997 |

* cited by examiner

*Primary Examiner*—Lisa Ann Douglas
(74) *Attorney, Agent, or Firm*—Wood, Herron & Evans, LLP

(57) ABSTRACT

A system for dispensing liquid material onto a moving substrate includes a liquid dispenser fluidly connected to a source of liquid material and a source of pressurized air. The liquid dispenser includes a pair of outer liquid material outlets and a plurality of inner liquid material outlets therebetween spaced along a common axis at one end of the dispenser for dispensing a plurality of strands of liquid material toward the substrate. The liquid dispenser further includes a pair of air outlets associated with each of the inner liquid material outlets and a single air outlet associated with each of the outer liquid material outlets for emitting pressurized air that is operable to oscillate the dispensed strands in directions predominantly parallel with the common axis of the liquid material outlets during flight toward the substrate to form an overlapping pattern of liquid material on the moving substrate. Methods for dispensing liquid material onto a moving substrate are also disclosed.

5 Claims, 10 Drawing Sheets

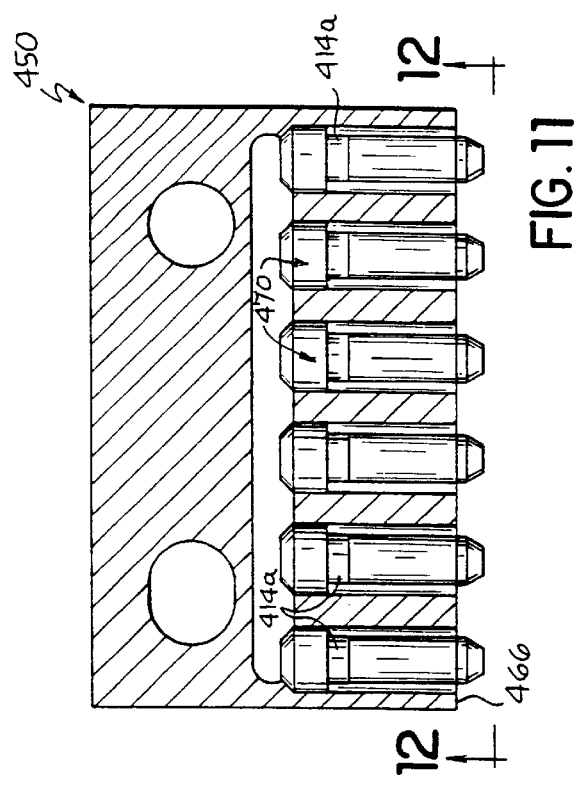
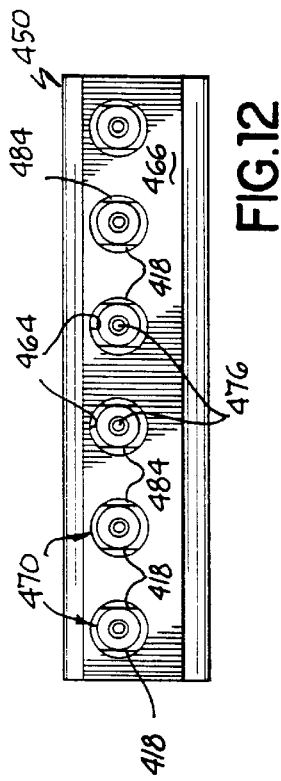
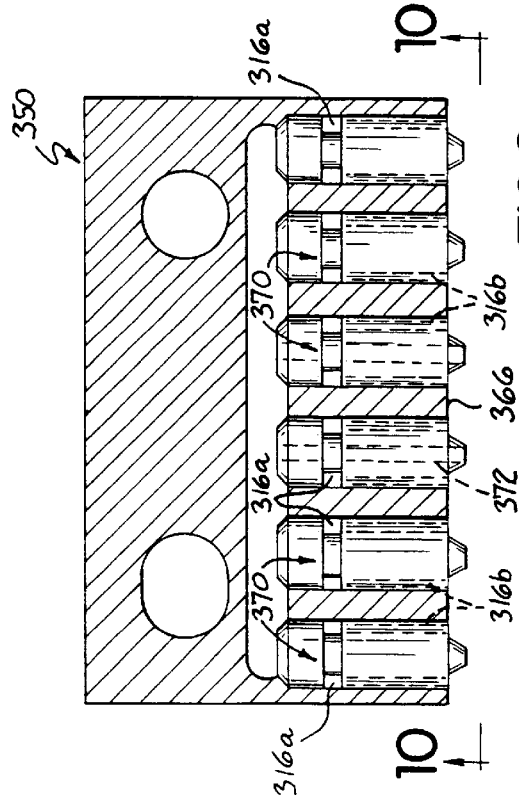
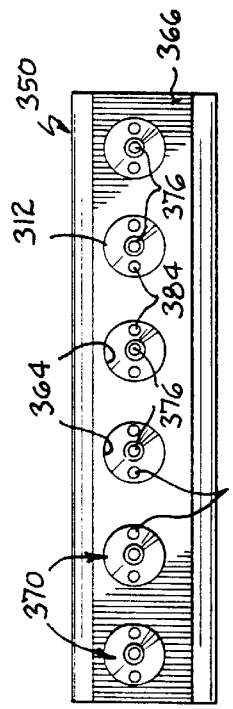

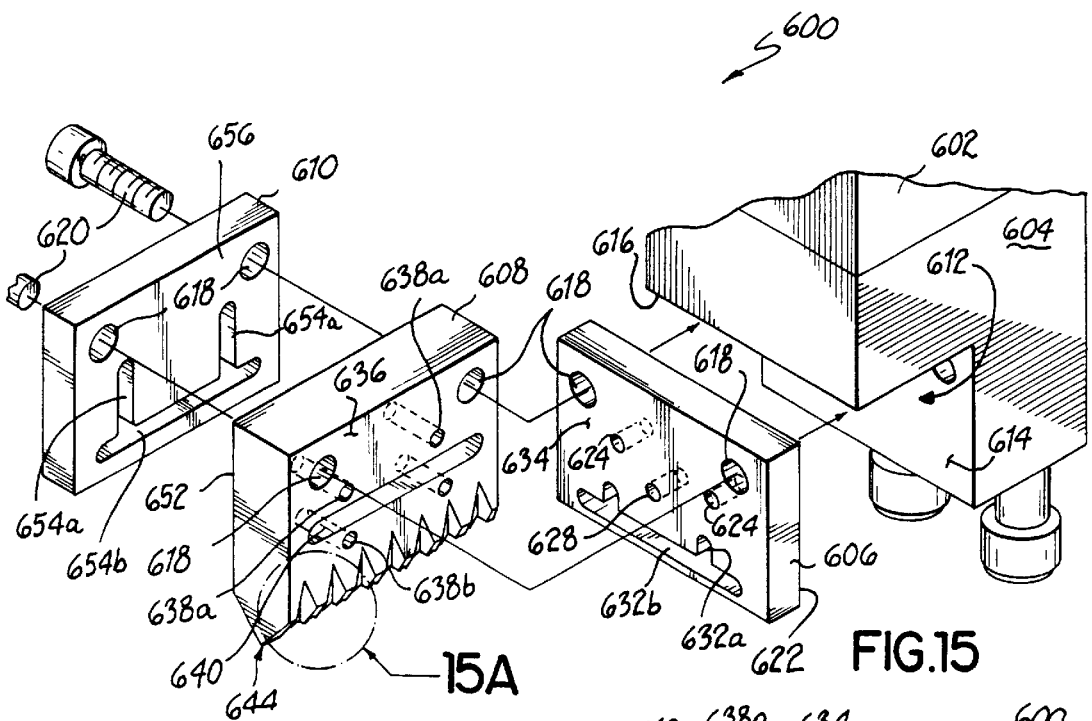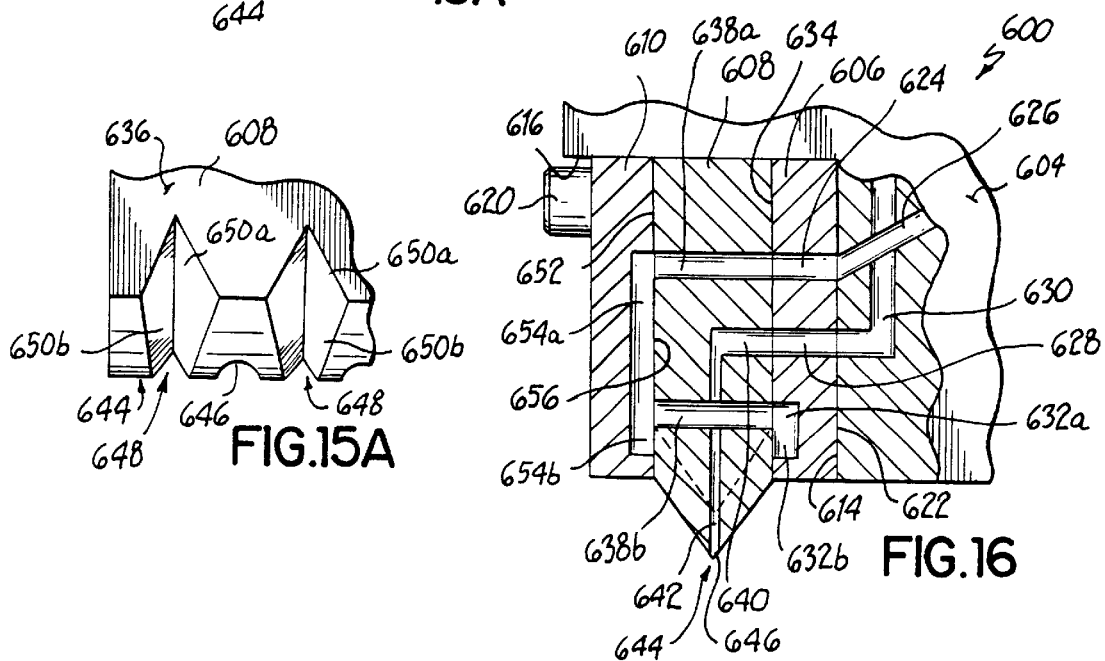

US 6,378,782 B1

METHOD AND APPARATUS FOR APPLYING A CONTROLLED PATTERN OF FIBROUS MATERIAL TO A MOVING SUBSTRATE

CROSS-REFERENCE

The present application is a continuation-in-part of copending application Ser. No. PCT/US99/08519, filed on Apr. 16, 1999, which claims the filing benefit of U.S. Ser. No. 60/082,069, filed on Apr. 17, 1998, each disclosure of which is hereby incorporated herein by reference in its entirety.

FIELD OF THE INVENTION

The present invention relates generally to material dispensing systems for applying material onto a substrate and, more particularly, to a material dispensing system having a modular die assembly for applying in a controlled manner patterns of fibrous material onto a moving substrate.

BACKGROUND OF THE INVENTION

Various dispensing systems have been used in the past for applying patterns of viscous material onto a moving substrate. In the production of disposable diapers, incontinence pads and similar articles, for example, hot melt adhesive dispensing systems have been developed for applying a laminating or bonding layer of hot melt thermoplastic adhesive between a non-woven fibrous layer and a thin polyethylene backsheet. Typically, the hot melt adhesive dispensing system is mounted above a moving polyethylene backsheet layer and applies a uniform pattern of hot melt adhesive material across the upper surface width of the backsheet substrate. Downstream of the dispensing system, a non-woven layer is laminated to the polyethylene layer through a pressure nip and then further processed into a final usable product.

In one known hot melt adhesive dispensing system, continuous beads or strands of adhesive are emitted from a multiple adhesive outlet die with multiple air jets oriented around the circumference of each material outlet. The multiple air jets drive air tangentially relative to the orientation of the adhesive strand as it emits from the die orifice, thereby attenuating each adhesive strand and causing the strands to swirl before being deposited on the upper surface of the moving substrate.

More recently, manufacturers of diaper products and others have been interested in small fiber technology for the bonding layer of hot melt adhesive in non-woven and polyethylene sheet laminates. To this end, hot melt adhesive dispensing systems have incorporated slot nozzle dies with a pair of angled air channels formed on either side of the elongated extrusion slot of the die. As the hot melt adhesive emits from the extrusion slot as a continuous sheet or curtain, pressurized air is emitted as a pair of curtains from the air channels to impinge upon, attenuate and fiberize the adhesive curtain to form a uniform fibrous web of adhesive on the substrate. Recently, fibrous web adhesive dispensers have incorporated intermittent control of adhesive and air flows to form discrete patterns of fibrous adhesive layers with well defined cut-on and cut-off edges and well defined side edges.

Meltblown technology has also been adapted for use in this area to produce a hot melt adhesive bonding layer having fibers of relatively small diameter. Meltblow dies typically include a series of closely spaced adhesive nozzles that are aligned on a common axis across the die head. A pair of angled air channels are formed on either side of the adhesive nozzles to extend parallel to the common nozzle axis. As hot melt adhesive emits from the series of aligned nozzles, pressurized air is emitted from the air channels as a pair of curtains that impinge upon, draw down and attenuate the fibers before they are applied to the moving substrate.

While meltblown technology has been used to produce fibrous adhesive layers on moving substrates, it has several drawbacks. As those skilled in the art will appreciate, meltblown technology typically uses a high volume of high velocity air to draw down and attenuate the emitted adhesive strands. The high velocity air causes the fibers to oscillate in a plane that is generally aligned with the movement of the substrate, i.e., in the machine direction. To adequately blend adjacent patterns of adhesive to form a uniform layer on the substrate, meltblow dispensers require the nozzles to be closely spaced. Moreover, the volume and velocity of the air must be high enough to sufficiently agitate and blend adjacent fibers.

However, the high volume of air used in meltblown dispensers adds to the overall operational cost as well as reduces the ability to control the pattern of emitted fibers. One byproduct of the high velocity air is "fly" in which the fibers get blown away from the desired deposition pattern. The "fly" can be deposited either outside the desired edges of the pattern, or even build up on the dispensing equipment which can cause operational problems that require significant maintenance. Another byproduct of the high velocity air and closely spaced nozzles is "shot" in which adjacent adhesive fibers become entangled and form globules of adhesive on the backsheet substrate. "Shot" is undesirable as it can cause heat distortion of the delicate polyethylene backsheet.

It will further be appreciated by those skilled in the art that the construction of the meltblow dies, with the continuous sheets of air formed on either side and parallel to the aligned nozzles, reduces the ability of manufacturers to modularize the meltblow dies in side-by-side fashion across the width of a moving substrate. The curtains of air are interrupted between adjacent melt blow dies which generally results in a less consistent fiber pattern on the substrate.

Additionally, the many closely spaced nozzles required in meltblow dies not only adds to manufacturing costs, but also forces lower material flow rates through each nozzle. Lower material flow rates per nozzle generally results in a greater variation of the fibers emitted from the nozzles. Moreover, the nozzles are typically more likely to clog at the lower material flow rates.

Thus, there is a need for a material dispensing system that improves control of dispensed material to form patterns on a moving substrate without "fly" or "shot". There is also a need for a material dispensing system that reduces costs associated with operation and maintenance. There is yet another need for a material dispensing system that improves the ability to modularize the dispensing system to provide a wider range of uniform material pattern widths across a moving substrate.

SUMMARY OF THE INVENTION

The present invention overcomes the foregoing and other shortcomings and drawbacks of the material dispensing systems and methods heretofore known. While the invention will be described in connection with certain embodiments, it will be understood that the invention is not limited to these embodiments. On the contrary, the invention includes all alternatives, modifications and equivalents as may be included within the spirit and scope of the present invention.

The present invention is directed to a material dispensing system and method for use in applying in a controlled manner a fibrous material in a desired pattern on a moving substrate. The material dispensing system has a source of fluid material to be applied and a source of pressurized air that are connected to a material dispensing head. The material dispensing head has a fluid manifold connected to the source of material, an air manifold connected to the source of pressurized air, and a dispensing module having an upper dispensing body and a lower modular die assembly mounted to one end of the dispensing body. The dispensing body is connected to the fluid manifold for delivering fluid in a controlled manner to the die assembly. The modular die assembly includes a series of aligned material outlets that emit the fluid in a series of spaced strands toward a substrate. The dispensing body is connected to the air manifold for delivering pressurized air in a controlled manner to the die assembly. The pressurized air is used to draw down and attenuate the strands to form fibers that oscillate in a generally transverse plane relative to the direction of travel of the moving substrate. The oscillation of the fibers provides a uniform pattern of fibrous material on the moving substrate. The pressurized air between the material outlets also separates the strands during the critical draw down phase to prevent entanglement of adjacent strands. The orientation of the air and material outlets in accordance with the principles of the present invention improves control of the dispensed material to form a desired pattern on the moving substrate.

In accordance with one aspect of the present invention, the modular die assembly has a die block mounted to a lower end of the dispensing body. The die block has a seat for mounting a pattern die and sealing plate to a lower end of the die block. Material passages are formed in the die block for delivering viscous material from the dispensing body to the pattern die. Air passages are also formed in the die block for delivering pressurized air from the air manifold to the pattern die. The sealing block is mounted to provide a seal between the various components of the modular die assembly.

The pattern die has a series of spaced openings that are preferably aligned on a common axis along a lower surface of the pattern die. A nozzle is preferably fitted into each spaced opening. The pattern die has material passages that communicate with the material passages in the die block for delivering the viscous material to the nozzles. The nozzles receive the viscous material from the material passages in the pattern die, and emit the material as spaced strands. The pattern die further includes a series of spaced air outlets that are also preferably aligned on a common axis along the lower surface of the pattern die. The pattern die air passages communicate with the air passages in the die block and provide pressurized air to the air outlets.

In accordance with a principle aspect of the present invention, the patten die includes a pair of outer liquid material outlets and a plurality of inner liquid material outlets therebetween spaced along a common axis at one end of the pattern die for dispensing a plurality of strands of liquid material toward the substrate. The pattern die further includes a pair of air outlets associated with each of the inner liquid material outlets and a single air outlet associated with each of the outer liquid material outlets for emitting pressurized air that is operable to oscillate the dispensed strands in directions predominantly parallel with the common axis of the liquid material outlets during flight toward the substrate to form an overlapping pattern of liquid material on the moving substrate.

In operation, the pattern die emits the viscous material preferably from the nozzles as spaced strands toward a surface of the moving substrate. The pattern die also emits air generally between the strands to draw down and attenuate the strands into small fibers that are deposited uniformly onto the moving substrate.

The orientation of the material outlets and air outlets in accordance with the principles of the present invention preferably causes the fibers to oscillate in a generally cross-machine direction that improves blending of adjacent fibers. The air between the material outlets also prevent entanglement of adjacent strands during the critical draw down phase to reduce "shot" formation on the moving substrate. Additionally, the orientation of the material outlets and air outlets requires less volume and velocity of air to create a uniform pattern of fibrous on the web. With less volume and velocity of air, the material dispensing system reduces undesirable "fly" formation and lowers operational and maintenance costs of the material dispensing system. Moreover, the orientation and operation of the material outlets and air outlets improves the ability to modularize the dispensing system to provide a wider range of uniform pattern widths across a moving substrate.

BRIEF DESCRIPTION OF THE DRAWING

The accompanying drawings, which are incorporated in and constitute a part of this specification, illustrate embodiments of the invention and, together with a general description of the invention given above, and the detailed description of the embodiments given below, serve to explain the principles of the invention.

FIG. 9 is a view similar to FIG. 3, illustrating a pattern die in accordance with a fourth embodiment of the present invention;

FIG. 10 is a bottom view of the pattern die illustrated in FIG. 9, taken along line 10—10 of FIG. 9;

FIG. 11 is a view similar to FIG. 3, illustrating a pattern die in accordance with a fifth embodiment of the present invention;

FIG. 12 is a bottom view of the pattern die illustrated in FIG. 11, taken along line 12—12 in FIG. 11;

FIG. 15 is an exploded view of a modular die assembly in accordance with a third embodiment of the present invention;

FIG. 15A is an enlarged view, in elevation, of the encircled area 15A in FIG. 15;

FIG. 16 is a cross-sectional view of the modular die assembly of FIG. 15 fully assembled, showing mounting of the various die components

DETAILED DESCRIPTION OF THE PREFERRED EMBODIMENTS

Figure 1A:
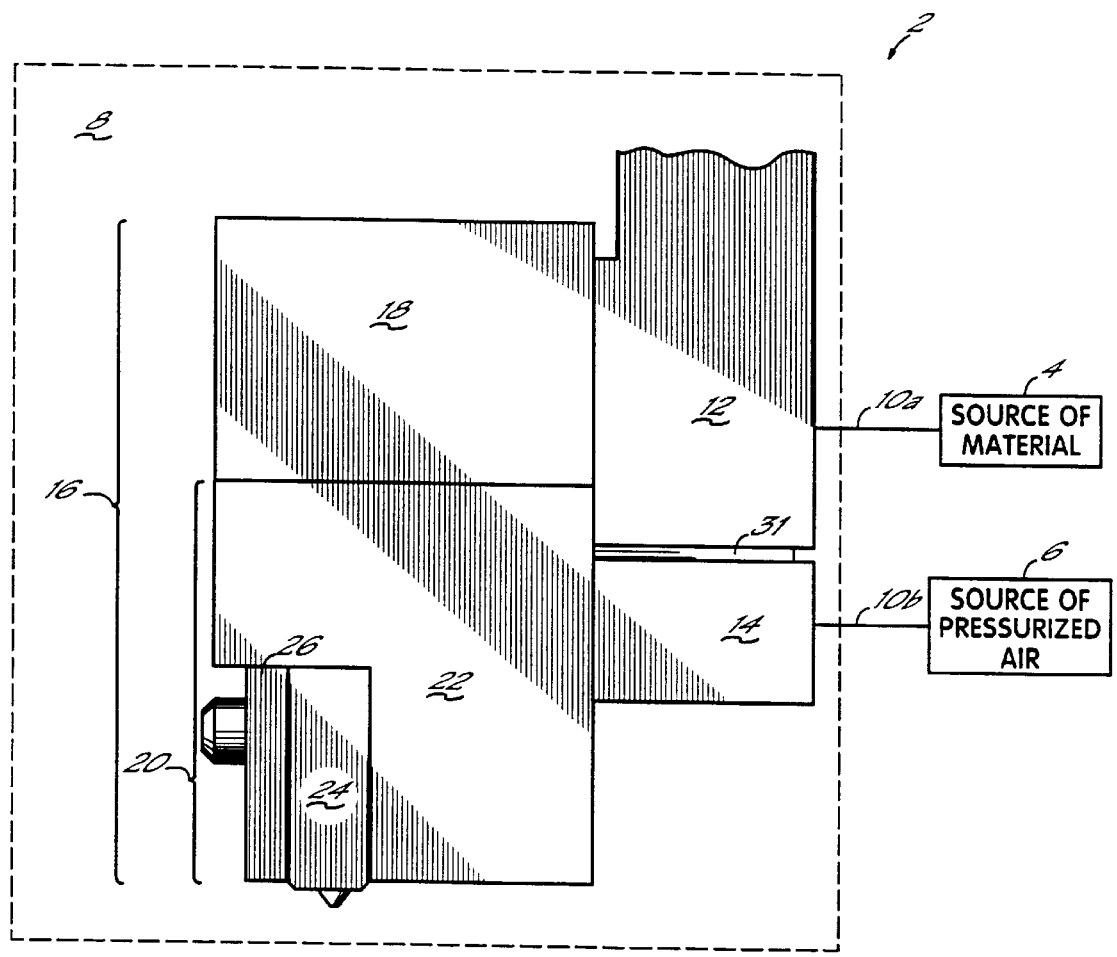
FIG. 1A is a functional block diagram of a material dispensing system in accordance with the principles of the present invention.

Referring now to the figures, and to FIG. 1A in particular, an overall material dispensing system 2 in accordance with the principles of the present invention is shown for dispensing a pattern of material on a moving substrate. For purposes of simplifying description of the present invention, the preferred embodiment will hereinafter be described in relation to the dispensing of hot melt thermoplastic adhesives, but those skilled in the art will readily appreciate application of the present invention to dispensing of other materials as well such as polymer and rubber based sealants and adhesive based materials. Material dispensing system 2 includes a source of material 4 and a source of pressurized air 6 that are each connected to a material dispensing head 8 through suitable delivery hoses or conduits 10a and 10b, respectively. Material source 4 may be, for example, an unloader and melter having a suitable hopper, melting grid and pump for delivering heated, viscous hot melt adhesive to the material dispensing head 8. Air source 6 may be a compressor or other suitable device for delivering pressurized air to the material dispensing head 8 as will be appreciated by those skilled in the art.

Material dispensing head 8 preferably has a fluid manifold 12 connected to the source of material 4 through hose 10a, and an air manifold 14 connected to the source of pressurized air 6 through hose 10b. A dispensing module 16 is provided having an upper dispenser body 18 mounted to the fluid manifold 12, and a lower modular die assembly 20 mounted to a lower end of the dispenser body 18. Die assembly 20 preferably includes a die block 22, a pattern die 24 and a sealing plate 26 that cooperate for purposes to be described in detail below. In operation, the dispenser body 18 receives viscous material from the fluid manifold 12 and delivers it in a controlled manner to the die assembly 20. Die assembly 20 also receives pressurized air from the air manifold 14 and is operable to apply the viscous material as a fibrous pattern on a moving substrate as described in detail below. Of course, the source of pressurized air 6 could also be connected to dispensing body 18 and then to the die assembly 20.

Figure 1B:
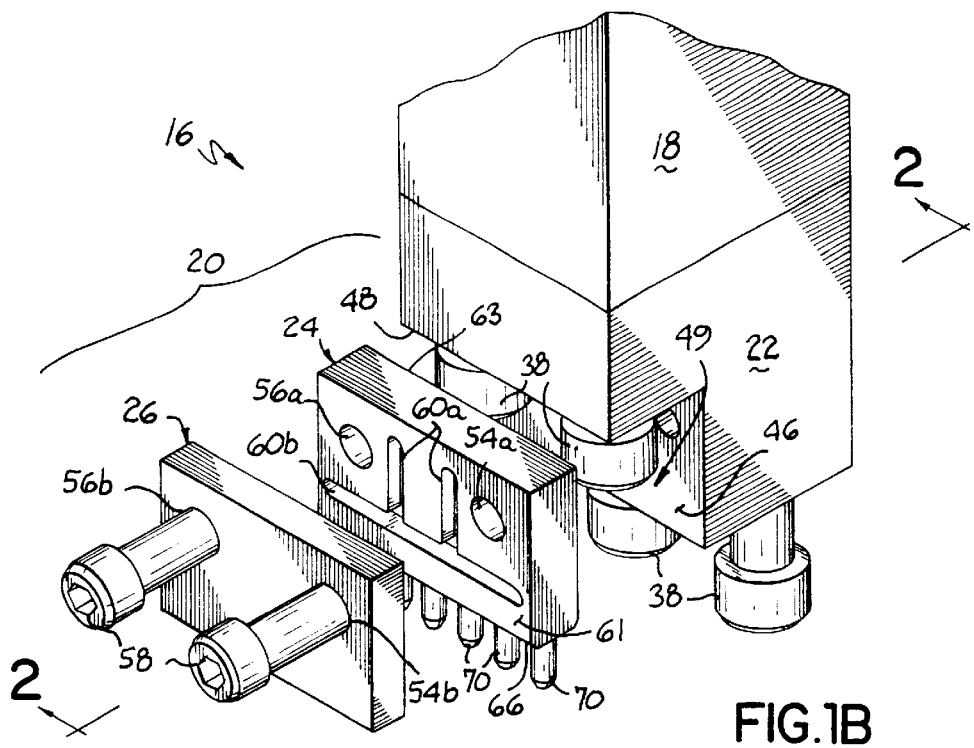
FIG. 1B is an exploded view of a modular die assembly in accordance with the principles of the present invention showing the die assembly mounted on a lower end of a material dispensing body.
Figure 3:
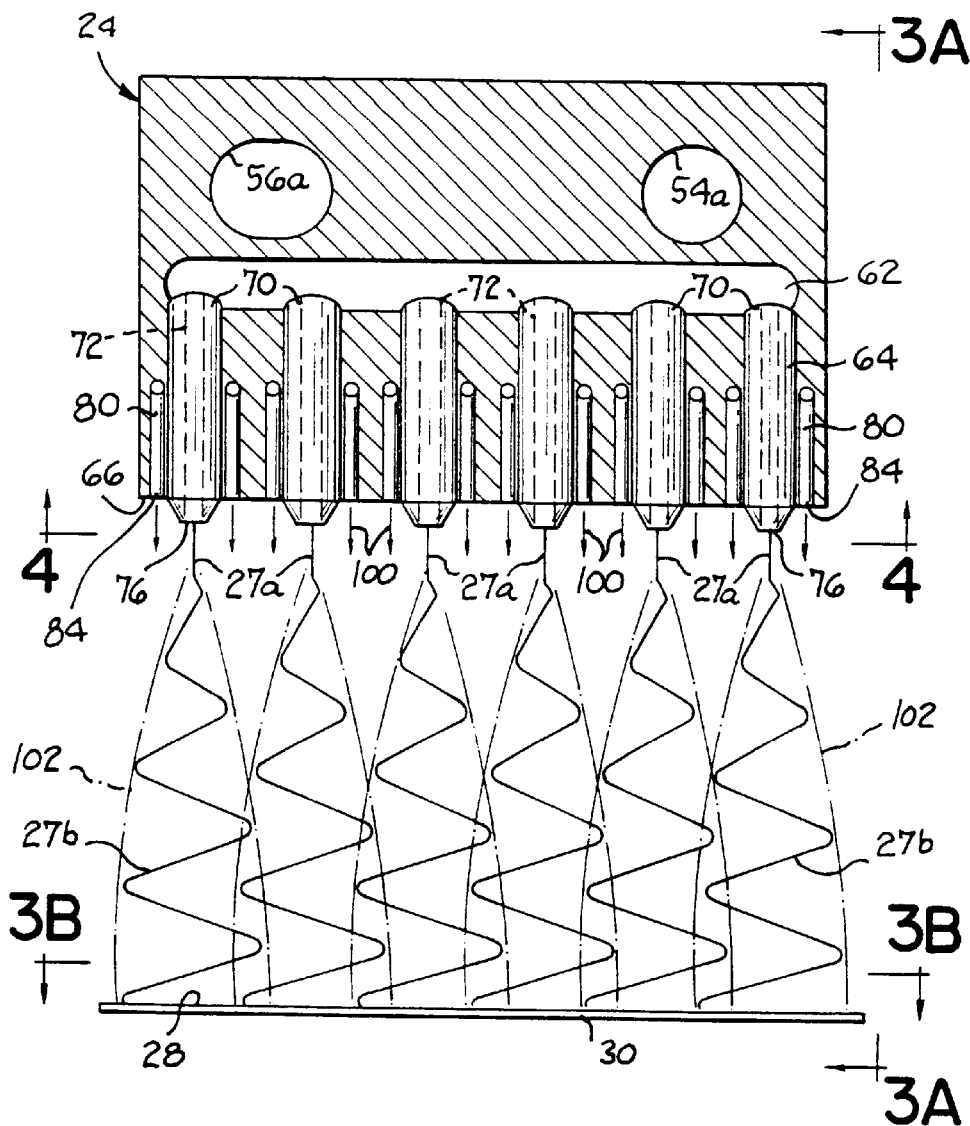
FIG. 3 is a cross-sectional view, taken along line 3—3 of FIG. 2, illustrating a pattern die in accordance with one embodiment of the present invention, and the material dispensing pattern created by the die assembly across the width of a moving substrate.

With reference to FIG. 1B, the die assembly 20 is shown in greater detail mounted to a lower end of dispenser body 18 in accordance with the principles of the present invention. As will be described in more detail below, die assembly 20 is particularly adapted to emit plural strands 27a of hot melt adhesive that are drawn down and attenuated into fibers 27b for deposition on a surface 28 of a moving substrate 30 (FIG. 3). As used herein, the term "fibrous material" refers to viscous material that is emitted from one or more material outlets in strand form, and which strands are drawn down or attenuated by pressurized air to form smaller diameter fibers. The fibers 27b can be of almost any diameter, but for hot melt adhesive applications, the diameters are typically in the range of 200 microns or less. It will be appreciated that other diameters are possible depending on the specific dispensing application.

Figure 2:
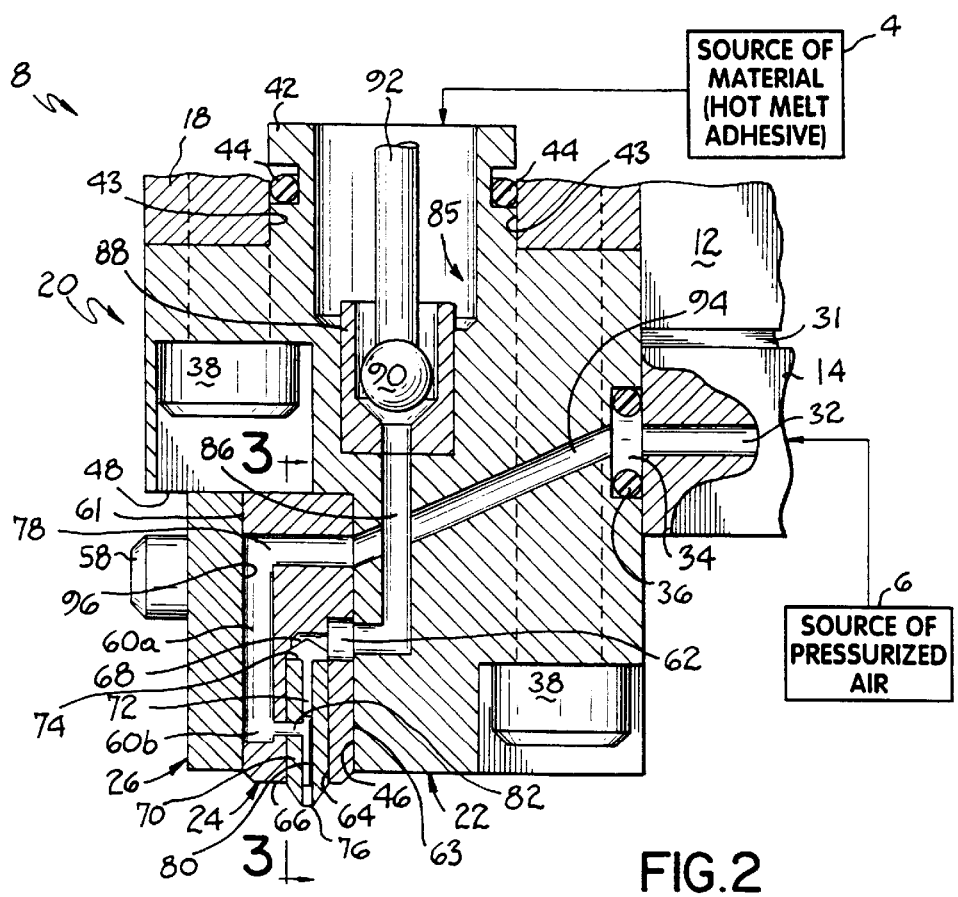
FIG. 2 is a cross-sectional view, taken along line 2—2 of FIG. 1B, showing one embodiment of the die assembly, and mounting of the various die assembly components.

As best understood with reference to FIG. 2, dispenser body 18 is adapted to provide a controlled continuous or intermittent flow of hot melt adhesive to the die assembly 20. Dispenser body 18 is mounted to the heated fluid manifold 12, and includes an adhesive cavity (not shown) for receiving viscous hot melt adhesive from the manifold 12. The air manifold 14 is mounted to a lower end of the fluid manifold 12 through fasteners (not shown) that extend through a spacer 31 mounted between the fluid and air manifolds 12 and 14, respectively. The air manifold 14 is formed with an air inlet line 32 fluidly connected to an air connector bore 34 formed in the die block 22. Pressurized air source 6 is fluidly connected to the air inlet line 32 for providing controlled, continuous or intermittent air supply to the air connector bore 34 formed in the die block 22. An O-ring 36 forms a fluid-tight seal between the die block 22 and the air manifold 14 at the junction of the air inlet line 32 and air connector bore 34. It will be appreciated that while fluid manifold 12 and air manifold 14 are shown as separate components, they could be combined as a single unit. It will be further appreciated that the adhesive and air could be continuous or intermittent depending on the specific dispensing application.

As shown with further reference to FIG. 2, the modular die assembly 20 is mounted to the lower end of the dispenser body 18 via four fasteners 38 that extend through unthreaded bores (not shown) formed in the die assembly 20. At their threaded ends, the set of fasteners 38 are connected to threaded bores (not shown) formed in the lower end of the dispenser body 18. The dispenser body 18 is heated by conduction via its contact with fluid manifold 12, and the die assembly 20 is heated by conduction via its contact with the dispenser body 18. Dispenser body 18 is preferably a Model H200 hot melt adhesive dispenser commercially available from Nordson Corporation of Westlake, Ohio. The details of the structure and operation of Nordson's H200 hot melt adhesive dispenser may be found in U.S. Pat. Nos. 4,801, 051 and 5,277,344, each of which is incorporated herein by reference in its entirety. The structure of the adhesive manifold 12, air manifold 14 dispenser body 18 can assume any form without departing from the principles and scope of the present invention, and are discussed briefly herein for purposes of background only. It will be appreciated by those of ordinary skill in the art that while die assembly 20 is shown mounted to a lower end of dispenser body 18, other mounting locations of die assembly 20 on dispenser body 18 are possible without departing from the spirit and scope of the present invention.

As shown with reference to FIGS. 1A–4, the die assembly 20 includes various die components that are collectively mounted to the lower end of the dispenser body 18 via the set of fasteners 38. Preferably, the die assembly 20 includes the die block 22 having a mounting end 42 (FIG. 2) for fluidly connecting the die assembly 20 to the dispenser body 18. The mounting end 42 extends into the adhesive cavity (not shown) of the dispenser body 14, and is sealed with walls 43 of the adhesive cavity via an O-ring 44. Die block 22 includes a vertical wall or surface 46 and a horizontal wall or surface 48 that define a seat 49 for mounting the pattern die 24 and sealing plate 26 to a lower end of the die block 22, as best understood with reference to FIGS. 1A–2. Pattern die 24 and sealing plate 26 include respective apertures 54a, 54b, and slots 56a, 56b extending through the respective die components for receiving a pair of fasteners 58 that mount the components to the vertical wall 46 of die block 22. It will be appreciated by those of ordinary skill in the art that slots 56a, 56b formed through the pattern die and sealing plates 24 and 26 are provided to accommodate for thermal expansion of the various die components caused by heat generated during the hot melt adhesive dispensing process.

With further reference to FIGS. 1B and 2, pattern die 24 preferably includes a series of elongated, vertically and horizontally oriented air distribution channels 60a and 60b formed on one face 61 of the pattern die, and an elongated, horizontally oriented adhesive distribution channel 62 formed on the other face 63 of the pattern die for purposes to be described in detail below. Pattern die 24 preferably includes six (6) bores 64 formed through a lower surface 66 of the pattern die that extend upwardly and fluidly connect with six (6) transverse passages 68 (one shown in FIG. 2) extending horizontally inwardly from the elongated adhesive distribution channel 62. Bores 64 preferably have a circular cross-section and are preferably aligned along an axis that is generally parallel to the longitudinal axis of the pattern die 24. The bores 64 are also preferably spaced equidistantly along the lower surface 66 of the pattern die 24. Bores 64 are sized to receive respective tubular nozzle inserts 70 that are inserted and frictionally engaged within the bores 64. Each nozzle insert 70 has an elongated adhesive passage 72 that extends generally along the longitudinal axis of the nozzle insert. Each adhesive passage 72 preferably has a uniform cross-sectional shape between an upper surface 74 of the nozzle insert 70 and a conically-shaped material outlet 76 formed at a lower end of each nozzle insert 70 that extends below the lower surface 66. It will be appreciated by those of ordinary skill in the art that adhesive passage 72 could be tapered without departing from the spirit and scope of the present invention. While adhesive passages 72 and material outlets 76 are shown having circular cross-sectional shapes, it is contemplated that square, rectangular or other cross-sectional shapes are possible for adhesive passages 72 and material outlets 76 without departing from the spirit and scope of the present invention. While six (6) bores 64 and six (6) nozzle inserts 70 are shown, it will be appreciated that fewer or more bores and nozzle inserts are possible depending on a specific material dispensing application. Moreover, it will be appreciated that while nozzle inserts 70 are preferred, they may be replaced with a series of adhesive passages drilled or otherwise formed in the lower surface 66 of pattern die 24.

Pattern die 24 further preferably includes a pair of transverse passages 78 (one shown in FIG. 2) extending through the pattern die that fluidly connect with the respective pair of vertically oriented air distribution channels 60a. The pair of vertically oriented air distribution channels 60a are fluidly connected to the horizontally oriented air distribution channel 60b formed on the one face 61 of the pattern die 24 (FIGS. 1B–2).

Figure 4:
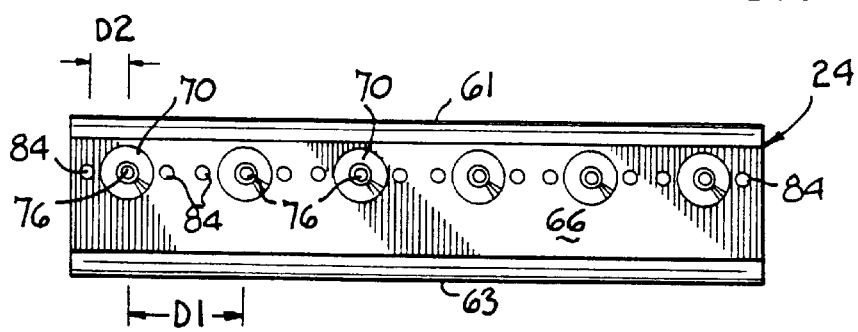
FIG. 4 is a bottom view of the pattern die illustrated in FIG. 3, taken along line 4—4 of FIG. 3.

In accordance with one embodiment of the present invention as shown with reference to FIGS. 2–4, the pattern die 24 includes a series of twelve (12) air passages 80 formed through the lower surface 66 of the pattern die that extend upwardly and fluidly connect with twelve (12) transverse passages 82 (one shown in FIG. 2) extending horizontally inwardly from the horizontally oriented air distribution channel 60b. Air passages 80 form air outlets 84 on the lower surface 66 of pattern die 24 that are preferably grouped in pairs in association with each material outlet 76. In this preferred arrangement, it will be appreciated by those of ordinary skill in the art that for six (6) material outlets 76, twelve (12) air passages 80 and twelve (12) transverse passages 82 are required. If the number of material outlets 76 increases or decreases, the number of air passages 80 and transverse passages 82 increases or decreases as well.

Preferably, the air passages 80 and air outlets 84 formed in association with the material outlets 76 are aligned generally along the axis of the material outlets 76, with each pair of air outlets 84 being positioned on opposite sides of a respective material outlet 76 for purposes to be described in more detail below. While air passages 80 and air outlets 84 are shown having circular cross-sectional shapes, it is also contemplated that square, rectangular or other cross-sectional shapes are possible for air passages 80 and air outlets 84 without departing from the spirit and scope of the present invention.

It will be appreciated that while air passages 80 are shown as extending in pairs along the longitudinal length of the nozzle inserts 70, the vertical orientation of the air outlets 84 may be changed without departing from the spirit and scope of the present invention. For example, each air passage 80 may angle inwardly toward the longitudinal axis of a respective nozzle insert 70. Alternatively, only the outermost air passages 80 on the lower surface 66 of pattern plate 24 may be angled inwardly to control side edge formation of the dispensed pattern. Additionally, while the air outlets 84 are preferably aligned on the same axis as the material outlets 76, other orientations of the air outlets 84 are possible that provide the same advantageous function of separating the strands 27a during the draw down phase and oscillating the fibers 27b in a generally cross-machine direction as described in detail below. For example, the air passages 84 may be staggered relative to the common axis of the material outlets 76 or positioned slightly off the common axis of the material outlets 76. Moreover, while a pair of air outlets 84 is preferred with each material outlet 76, more air outlets 84 per material outlet 76 are possible that provide the advantageous functions described herein.

As shown with reference to FIG. 2, die block 22 includes a stepped bore 85 and a supply passage 86 for delivering hot melt adhesive from the adhesive cavity (not shown) of dispenser body 18 to the elongated adhesive distribution channel 62 of pattern die 24. A valve seat 88, preferably made of carbide, is located in a lower portion of the stepped bore 85 that cooperates with a ball 90 formed on the lower end of a valve plunger 92 for providing controlled continuous or intermittent supply of hot melt adhesive to the adhesive distribution channel 62. In this way, hot melt adhesive may be applied to the surface 28 of moving substrate 30 with well-defined cut-on and cut-off edges through the material outlets 76 in accordance with the present invention as will be described in more detail below or as a continuous pattern. It will be appreciated by those of ordinary skill in the art that while a single supply passage 86 is shown, the supply passage 86 may include two or more branches (not shown) that fluidly communicate with adhesive distribution panel 62. In this configuration of the supply passage 86, it is contemplated that a single fastener 58 could be used to mount the pattern die 24 and sealing plate 26 to the die block 22.

With further reference to FIG. 2, die block 22 preferably includes a pair of air passages 94 (one shown) that extend between the air connector bore 34 and the respective pair of transverse passages 78 extending through the pattern die 24. In this way, the pressurized air source 6 fluidly connected to air inlet line 32 and air connector bore 34 delivers air through each of the air outlets 84 formed in the pattern die 24 during operation of the material dispensing head 8 as will be described in more detail below.

As shown with reference to FIG. 2, sealing plate 26 is mounted having a planar face 96 in engagement with face 61 of pattern die 24 via the fasteners 58. Pattern die 24 is mounted having opposite face 63 in engagement with vertical wall or surface 46 of die block 22. It will be appreciated that fasteners 58 must be applied with sufficient torque to provide the necessary fluid seals between the sealing plate 26, pattern die 24 and die block 22 to prevent loss of air or hot melt adhesive between the components of the modular die assembly 20.

Figure 3A:
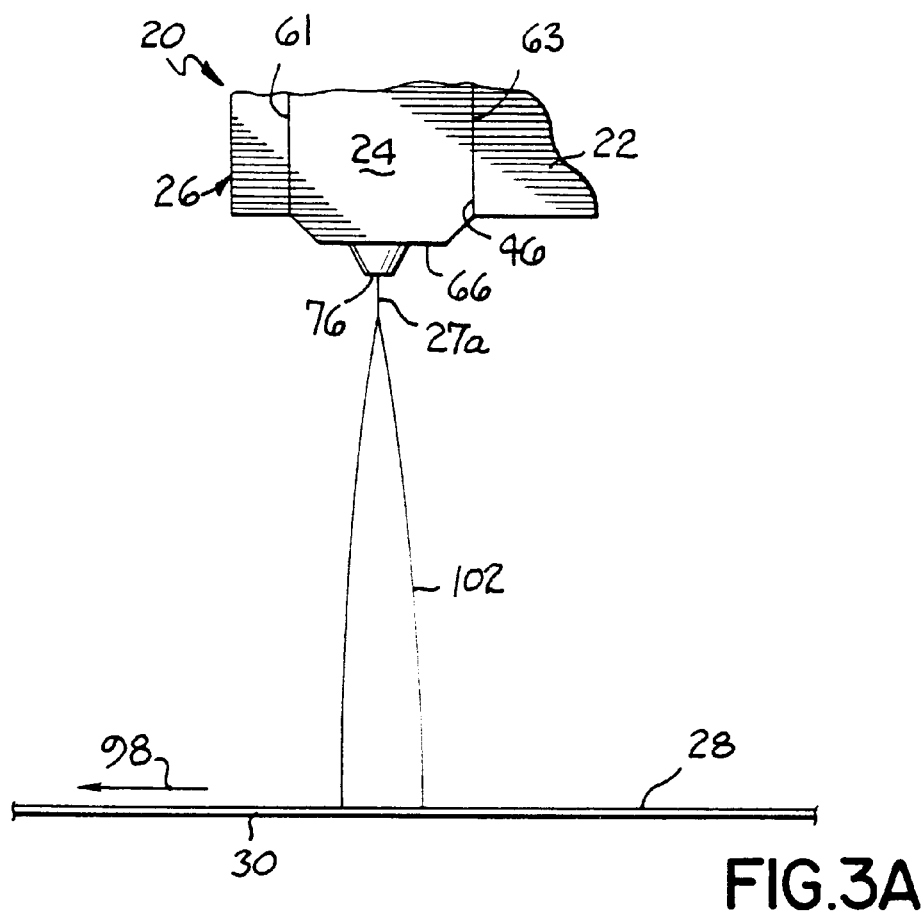
FIG. 3A is a side view, taken along line 3A—3A of FIG. 3, illustrating the material dispensing beam created by the die assembly.
Figure 3B:
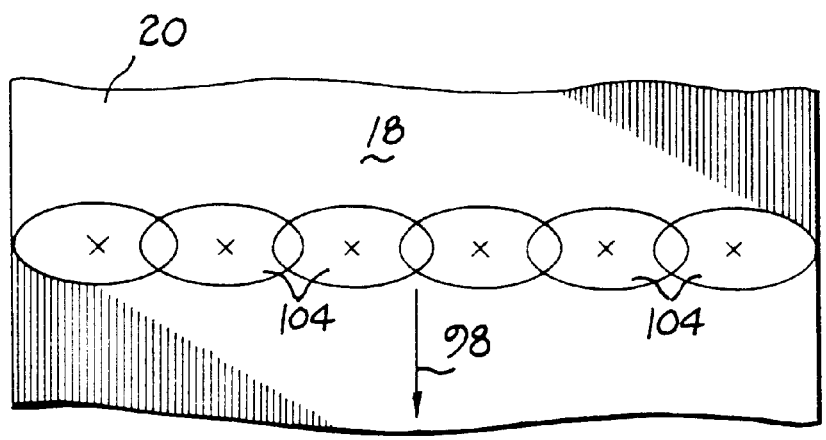
FIG. 3B is a diagrammatic top plan view, taken along line 3B—3B of FIG. 3, illustrating a material dispensing footprint created by the die assembly.

In operation of the material dispensing head 8, as best understood with reference to FIGS. 2–4, the die assembly 20 is mounted above the surface 28 of moving substrate 30 with its longitudinal axis positioned generally transverse to the direction of travel of the substrate 30 (represented by directional arrows 98 in FIGS. 3A and 3B). Dispenser body 18 introduces hot melt adhesive into an upper portion of the stepped bore 85 formed in the die block 22. With the ball 90 of valve plunger 92 in engagement with the valve seat 88, adhesive is prevented from flowing into supply passage 86 and through the series of aligned nozzle inserts 70. As the valve plunger 92 is forced upwardly during operation of the dispenser body 18 in a known manner to disengage ball 90 from seat 88, hot melt adhesive is directed along flow paths defined by the supply passage 86, adhesive distribution channel 62, transverse passages 68, and adhesive passages 72 formed in the nozzle inserts 70. The hot melt adhesive is emitted through the material outlets 76 of the nozzle inserts 70 as strands 27a that are directed toward the surface 28 of moving substrate 30. It will be appreciated by those skilled in the art that while a single dispensing module 16 is illustrated and described herein for applying fluid material such as hot melt adhesive on substrate 30, a series of dispensing modules 16, each with its associated dispenser body 18 and die assembly 20, may be mounted in side-by-side relationship to extend across a wide range of substrate widths and thereby provide a wide range of material dispensing pattern widths.

At the same time that hot melt adhesive is emitted through the material outlets 76 in strand form, pressurized air is directed along flow paths defined by the air passages 94, transverse passages 78, vertically oriented air distribution channels 60a, horizontally oriented air distribution channel 60b, transverse passages 82, and air passages 80 formed through the lower surface 66 of pattern die 24. The pressurized air is emitted through the air outlets 84 positioned on opposite sides of each material outlet 76, as represented diagrammatically by arrows 100 in FIG. 4.

Further referring to FIGS. 2, 3A, 3B, the pressurized air emitted from each pair of air outlets 84 associated with a respective material outlet 76 serves several functions. First, the pressurized air from each air outlet pair draws down and attenuates each strand 27a of hot melt adhesive as it emits from a material outlet 76. The attenuated strands 27a preferably form fibers 27b having a diameter of less than 200 microns on the surface 28 of the moving substrate 30 for hot melt dispensing applications. The pressurized air emitted from each air outlet 84 also serves to separate adjacent strands 27a during the critical draw down phase to reduce "shot" formation on the moving substrate 30. Moreover, the pressurized air serves to oscillate the fibers 27b generally in a plane defined by the air outlets 84 associated with each material outlet 76.

When the air outlets 84 are formed on the same axis as the material outlets 76, the pressurized air causes the fibers 27b to oscillate generally in a plane transverse to the travel direction 98 of moving substrate 30 (i.e., in a cross-machine direction). The strands 27a are emitted from respective material outlets 76 and form side-by-side fiber beams 102 (FIGS. 3 and 3A) that overlap along adjacent edges to define generally oval placement patterns 104 (FIG. 3B) of hot melt adhesive on the upper surface 28 of moving substrate 30. As each oval 104 has its longitudinal axis aligned generally transverse to the travel direction 98 of moving substrate 30, and as adjacent edges of the ovals 104 overlap, the deposited fibers 27b blend to form a uniform hot melt adhesive pattern across the upper surface 28 of moving substrate 30. While oval patterns 104 are shown as the preferred displacement pattern to form a small dispensing footprint for each material outlet 76, it will be appreciated that other pattern cross-section shapes are possible.

To achieve a preferred uniform pattern of adhesive on the moving substrate 30, a spacing is provided between adjacent material outlets 76, designated $D_1$ in FIG. 4, preferably within the range of about 0.050 and about 0.250 in. for hot melt adhesive applications. Spacing values less than the preferred lower limit of the range may cause adjacent strands 27a to interfere or entangle in an undesirable fashion, while values above the preferred upper limit of the range may not provide the necessary blending to achieve a uniform pattern. Most preferably, the spacing $D_1$ is within the range of about 0.100 and about 0.200 in. for hot melt adhesive applications.

A spacing is also provided between each air outlet 84 and its associated material outlet 76, designated $D_2$ in FIG. 4, preferably within the range of about 0.015 and about 0.080 in. for hot melt adhesive applications. Spacing values less than the preferred lower limit of the range may result in a less stable formation of fibers 27b, while values above the preferred upper limit of the range may not provide the necessary fiber oscillation amplitude to blend adjacent fibers 27b to achieve a uniform pattern. Most preferably, the spacing $D_2$ is within the range of about 0.030 and about 0.060 in. for hot melt adhesive applications.

When material outlets 76 are formed having circular cross-sectional shapes, a preferred diameter of the material outlets 76 is within the range of about 0.010 and about 0.030 in. for hot melt adhesive applications. Material outlet side diameters less than the preferred lower limit of the range may be susceptible to clogging, while diameters above the preferred upper limit of the range may not create sufficient backpressures necessary to produce consistent diameter fibers 27b on the substrate 30. Most preferably, the diameter of the material outlets 76 is within the range of about 0.016 and about 0.024 in. for hot melt adhesive applications. It will be appreciated that other cross-sectional shapes for the material outlets 76, such as square or rectangular cross-sectional shapes, and other diameters are possible without departing from the spirit and scope of the present invention.

When air outlets 84 are formed having a circular cross-sectional shape, a preferred diameter of the air outlets 84 is within the range of about 0.010 and about 0.050 in. for hot melt adhesive applications. Air outlet diameters less than the preferred lower limit of the range may not provide sufficient drawdown and formation of the fibers 27b, while diameters above the preferred upper limit of the range may not provide any further beneficial draw down or attenuation of the strands 27a. Most preferably, the diameter of the air outlets 84 is within the range of about 0.012 and about 0.030 in. for hot melt adhesive applications. It will be appreciated that other cross-sectional shapes for the air outlets 84, such as square, crescent or rectangular cross-sectional shapes, and other side dimensions are possible without departing from the spirit and scope of the present invention.

Figure 5:
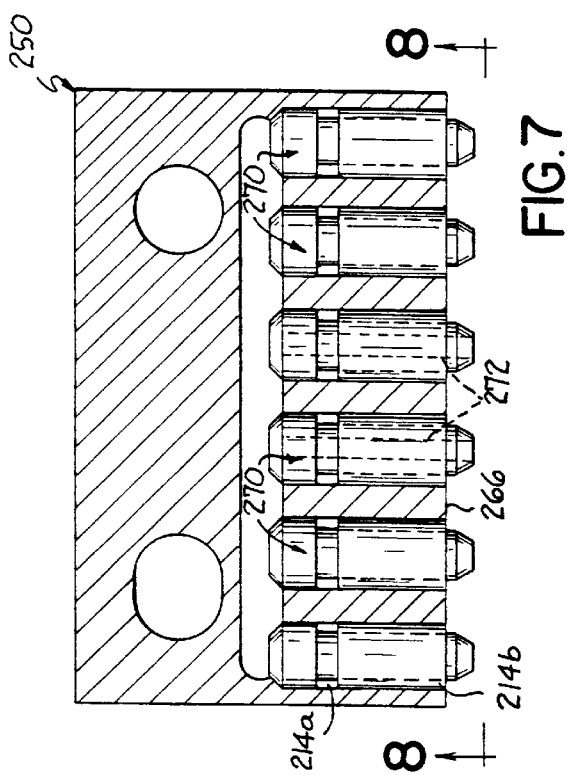
FIG. 5 is a view similar to FIG. 3, illustrating a pattern die in accordance with a second embodiment of the present invention.
Figure 6:
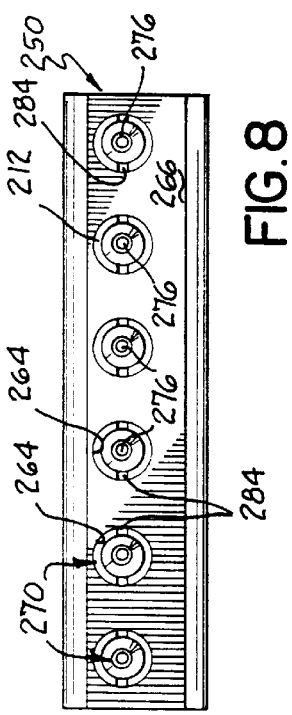
FIG. 6 is a bottom view of the pattern die illustrated in FIG. 5, taken along line 6—6 of FIG. 5.

In another embodiment of the present invention, as best understood with reference to FIGS. 5 and 6, a modified pattern die 150 is shown. All other components of the die assembly 20 are generally unchanged. In this embodiment, pattern die 150 preferably includes six (6) bores 164 formed through the lower surface 166 of the pattern die that extend upwardly and fluidly connect with the six (6) transverse passages (one shown in FIG. 2) extending horizontally inwardly from the adhesive distribution channel 62. The bores 164 are equidistantly spaced along the lower surface 166 and have a circular cross-section. The bores 164 are also preferably aligned along an axis that is generally parallel to the longitudinal axis of the pattern die. The bores 164 are sized to receive respective tubular inserts 170 that are inserted and frictionally engaged within the bores 164. Six (6) oblong bores 106 are formed through the lower surface 166 of the pattern die 150 that extend upwardly and fluidly connect with the twelve (12) transverse passages 82 (one shown in FIG. 2) extending horizontally inwardly from the horizontally oriented air distribution channel 60b. The oblong bores 106 are equidistantly spaced, and are preferably aligned with their respective longitudinal axes aligned along an axis that is also generally parallel to the longitudinal axis of the pattern die 150 and coincident with the axis of bores 164. In this way, crescent-shaped air outlets 184 are formed on opposite sides of each material outlet 176 by a wall 108 of the oblong bores 106 and an outer cylindrical surface 110 of the tubular inserts 170. The air outlets 184 and material outlets 176 function substantially as described in detail above to draw down and attenuate each strand 27a of hot melt adhesive as it emits from a material outlet 176. The spacing distance $D_2$ between each air outlet 184 and a respective material outlet 176 is defined by the thickness of the tubular wall 112 of the nozzle insert 170. It will be appreciated that the oblong bores 106 of this embodiment eliminate the need to form the twelve (12) air passages 80 associated with the pattern die 24 of FIGS. 1B–4, thereby simplifying overall manufacturing of the pattern die.

Figure 7:
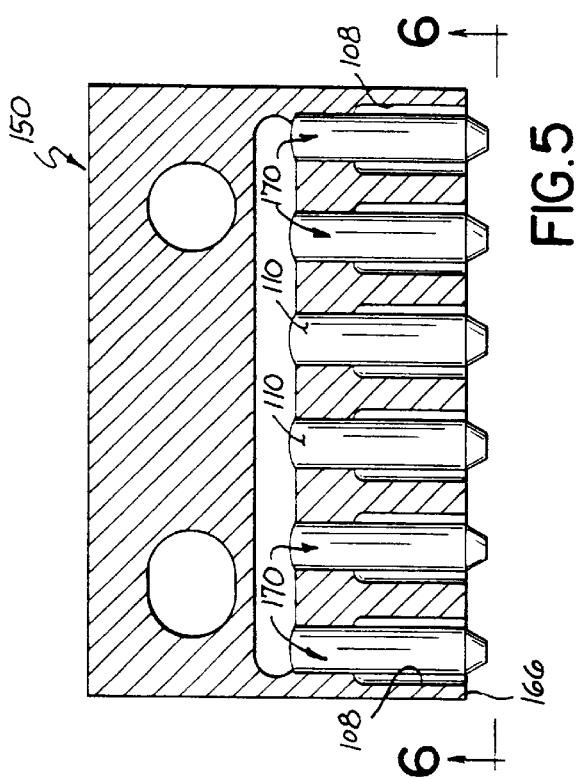
FIG. 7 is a view similar to FIG. 3, illustrating a pattern die in accordance with a third embodiment of the present invention.
Figure 8:
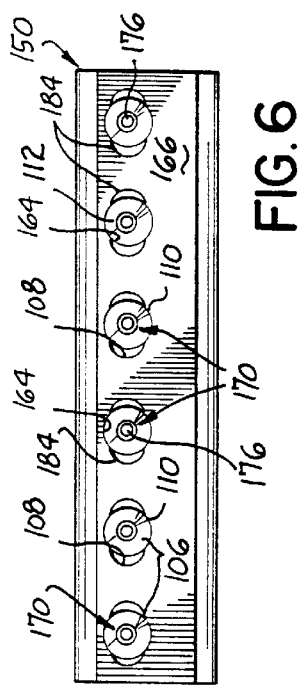
FIG. 8 is a bottom view of the pattern die illustrated in FIG. 7, taken along line 8—8 of FIG. 7.
Figure 7A:
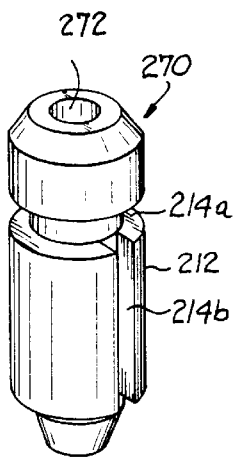
FIG. 7A is a perspective view of a nozzle insert shown in FIG. 7.

In another alternative embodiment of the present invention, as best understood with reference to FIGS. 7, 7A and 8, a modified pattern die 250 is shown. All other components of the die assembly 20 are generally unchanged. In this embodiment, the nozzle inserts 270 are slightly enlarged (FIG. 7A), and include an annular air channel 214a and a pair of elongated, recessed air channels 214b formed in the tubular wall 212 of the each nozzle insert 270. The nozzle inserts 270 are received and frictionally engaged in six (6) bores 264 formed through the lower surface 266 of the pattern die 250 as described in detail above. The annular air channels 214a fluidly communicate with six (6) transverse passages (not shown) extending horizontally inwardly from the horizontally oriented air distribution channel 60b and fluidly connected to the bores 264. Each pair of air channels 214b are preferably formed on opposite sides of each adhesive passage 272 extending through the nozzle insert 270. The nozzle inserts 270 are positioned in the six (6) bores 264 with each pair of air channels 214b forming a pair of air outlets 284 with a cylindrical wall of the bores 264. Preferably, each pair of air outlets 284 is formed on opposite sides of a respective material outlet 276, and air outlets 284 and material outlets 276 are aligned along an axis that is generally parallel to the longitudinal axis of the pattern die 250. The air outlets 284 and material outlets 276 function substantially as described in detail above to draw down and attenuate each strand 27a of hot melt adhesive as it emits from a material outlet 276. It will be appreciated that the tubular nozzle inserts 270 of this embodiment reduce the number of transverse passages 82 that need to be formed as well as eliminating the need to form the twelve (12) air passages 80 associated with the pattern die 24 of FIGS. 1A–4, thereby also simplifying overall manufacturing of the pattern die.

In yet another alternative embodiment of the present invention, as best understood with reference to FIGS. 9 and 10, a modified pattern die 350 is shown. All other components of the die assembly 20 are generally unchanged. In this embodiment, the nozzle inserts 370 are slightly enlarged and include an annular air channel 316a and a pair of elongated air channels 316b formed through the tubular wall 312 of the each nozzle insert 370. The nozzle inserts 370 are received and frictionally engaged in six (6) bores 364 formed through the lower surface 366 of the pattern die 350 as described in detail above. The air channels 316a fluidly communicate with six (6) transverse passages (not shown) extending horizontally inwardly from the horizontally oriented air distribution channel 60b and fluidly connected to the bores 364. Each pair of air channels 316b are preferably formed on opposite sides of the adhesive passage 372 extending through each nozzle insert 370. The nozzle inserts 370 are positioned in the six (6) bores 364 with each pair of air channels 316b forming a pair of air outlets 384 on opposite sides of a respective material outlet 376. Preferably, the air outlets 384 and material outlets 376 are aligned along an axis that is generally parallel to the longitudinal axis of the pattern die 350. The air outlets 384 and material outlets 376 function substantially as described in detail above to draw down and attenuate each strand 27a of hot melt adhesive as it emits from a material outlet 376. It will be appreciated that where the elongated air channels 316b are preformed in each nozzle insert 370, the air channels 316b are sealed off from the adhesive passage 372.

Figure 11A:
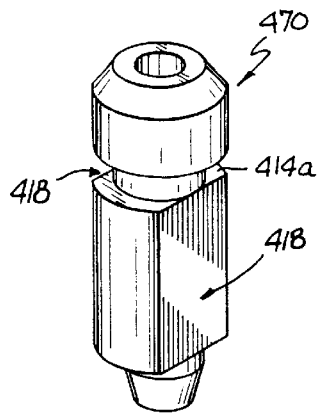
FIG. 11A is a perspective view of a nozzle insert shown in FIG. 11.

In still yet another alternative embodiment of the present invention, as best understood with reference to FIGS. 11, 11A and 12, a modified pattern die 450 is shown. All other components of the die assembly 20 are unchanged. In this embodiment, each air nozzle insert 470 includes an annular air channel 414a and a pair of planar faces 418 formed on opposite sides of the nozzle insert 470. The nozzle inserts 470 are received and frictionally engaged in six (6) bores 464 formed through the lower surface 466 of the pattern die 450. The annular air channels 414a fluidly communicate with six (6) transverse passages (not shown) extending horizontally inwardly from the horizontally oriented air distribution channel 60b and fluidly connected to the bores 464. The nozzle inserts 470 are positioned in the six (6) bores 464 with each planar face 418 forming a pair of air outlets 484 with a cylindrical wall of the bores 464. The air outlets 484 are formed on opposite sides of a respective material outlet 476, and the air outlets 484 and material outlets 476 are preferably aligned along an axis that is generally parallel to the longitudinal axis of the pattern die 450. The air outlets 484 and material outlets 476 function substantially as described in detail above to draw down and attenuate each strand 27a of hot melt adhesive as it emits from a material outlet 476.

Figure 13:
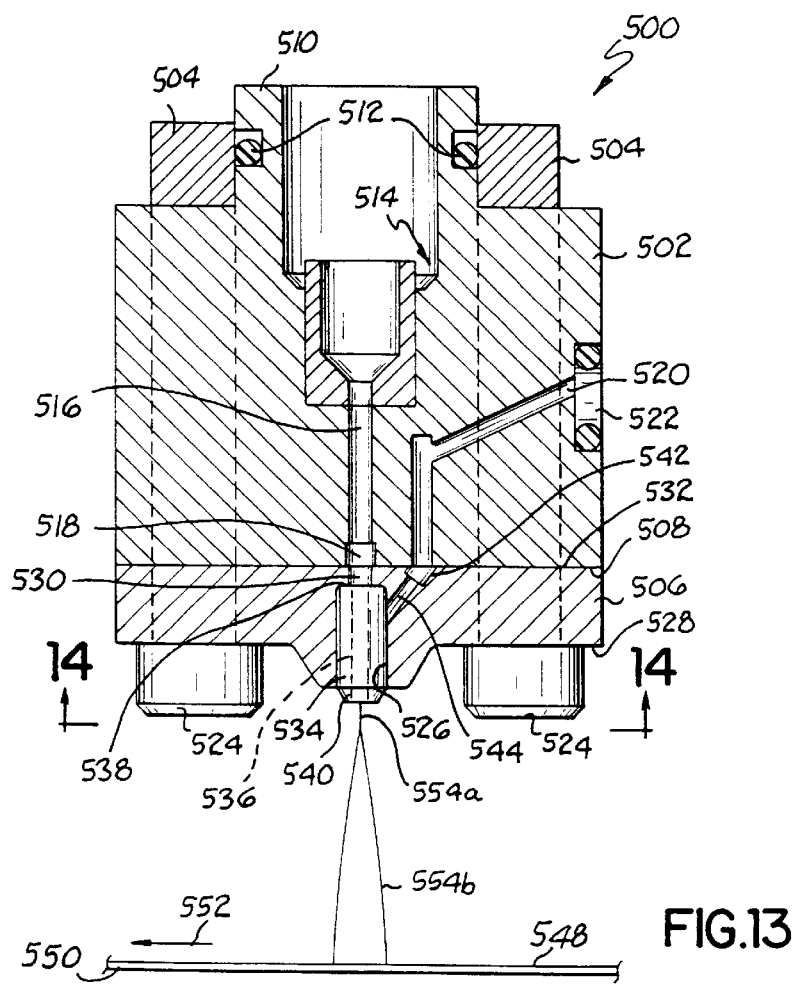
FIG. 13 is diagrammatic cross-sectional view of a modular die assembly in accordance with an alternative embodiment of the present invention.
Figure 14:
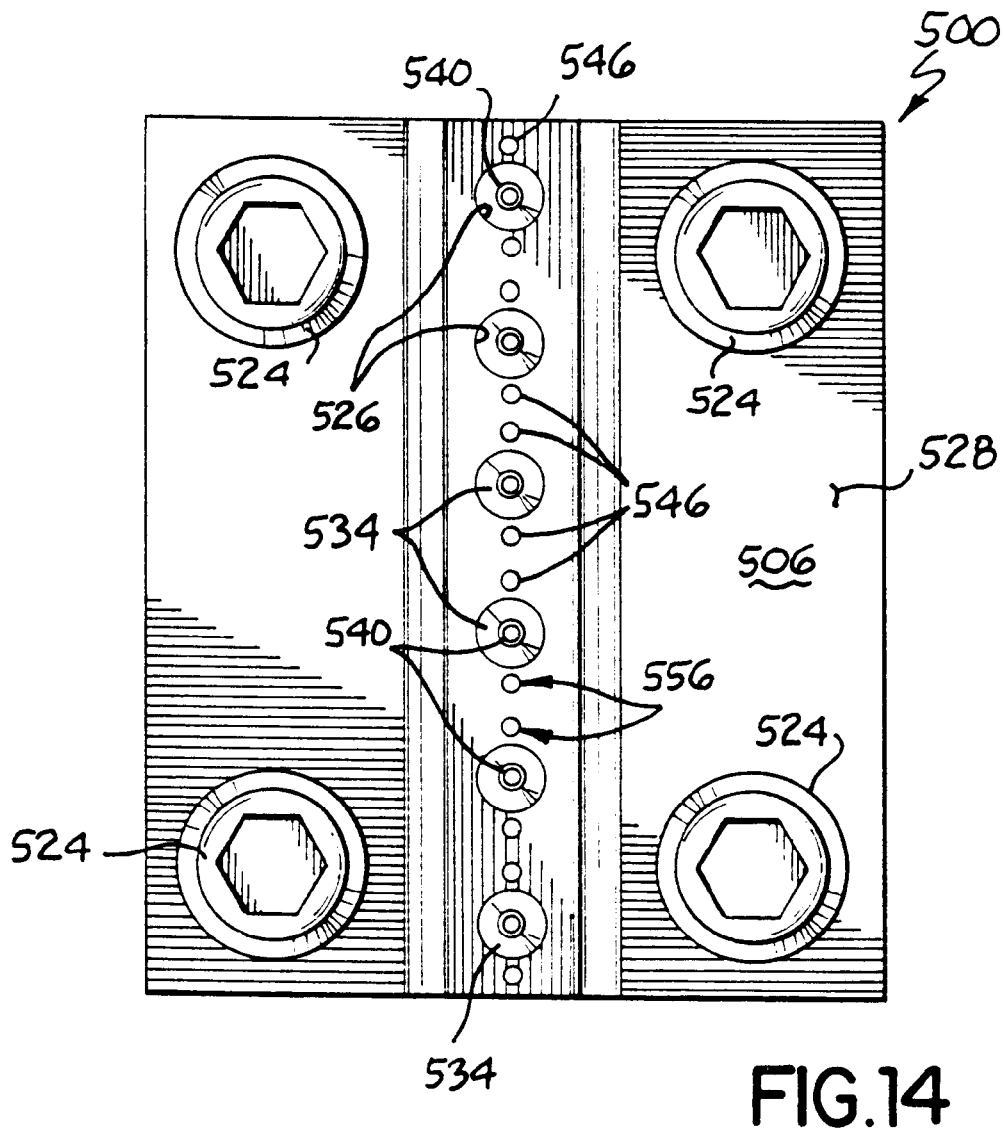
FIG. 14 is a bottom view of a pattern die illustrated in FIG. 13, taken along line 14—14 of FIG. 13.

Referring now to FIGS. 13 and 14, a modular die assembly 500 in accordance with an alternative embodiment of the present invention is shown. Die assembly 500 includes a die block 502 mounted to a lower end of a dispenser body 504, and a pattern die 506 mounted to a lower planar face 508 of the die block 502. It will be appreciated that the dispenser body 504 is similar in structure and operation to the dispenser body 18 described in detail above. Die block 502 has a mounting end 510 for fluidly connecting the die assembly 500 to the dispenser body 504. The mounting end 510 extends into the adhesive cavity (not shown) of the dispenser body 504, and is sealed with walls of the adhesive cavity via an O-ring 512.

Die body 502 has a stepped bore 514 and a supply passage 516 for delivering hot melt adhesive from the adhesive cavity to an elongated adhesive distribution channel 518 formed in the lower planar face 508 of the die body 502. A pair of air passages 520 (one shown in FIG. 13) is formed in the die body 502 to extend between an air connector bore 522 and the lower planar face 508 of the die body 502. A set of fasteners 524 extend through the die body 502 and pattern die 506 to mount the die assembly 500 to the dispenser body 504.

Pattern die 506 preferably includes a series of six (6) bores 526 (one shown in FIG. 13) formed through a lower surface 528 of the pattern die that extend upwardly and fluidly connect with six vertically oriented (6) passages 530 (one shown in FIG. 13) extending from an upper planar face 532 of the pattern die 506. Bores 526 preferably have a circular cross-section and are preferably aligned along an axis that is generally parallel to the longitudinal axis of the pattern die 506. The bores 526 are also preferably spaced equidistantly along the lower surface 528 of the pattern die 506, and are sized to receive respective tubular nozzle inserts 534 that are inserted and frictionally engaged within the bores 526. Each nozzle insert 534 has an elongated adhesive passage 536 that extends generally along the longitudinal axis of the nozzle insert. Each adhesive passage 536 preferably has a uniform cross-sectional shape between an upper surface 538 of the nozzle insert 534 and a conically-shaped material outlet 540 formed at a lower end of each nozzle insert 534 that extends below the lower surface 528 of pattern die 506. Of course, the adhesive passages 536 could be tapered within the spirit and scope of the present invention.

Pattern die 506 further preferably includes an elongated air distribution channel 542 formed in the upper face 532 of the die head. In accordance with one embodiment of the present invention, the pattern die 506 includes a series of twelve (12) passages 544 (one shown in FIG. 13) that are each fluidly connected at one respective end to the air distribution channel 542. The other respective ends of the passages 544 are fluidly connected to twelve (12) air passages 546 (FIG. 14) that are formed through the lower surface 528 of the pattern die 506.

In operation, the die assembly 500 is mounted above a surface 548 of a moving substrate 550 with its longitudinal axis positioned generally transverse to the direction of travel of the moving substrate 550 (represented by directional arrow 552 in FIG. 13). Dispenser body 504, similar to dispenser body 18 described in detail above, introduces hot melt adhesive into an upper portion of the stepped bore 514 formed in the die body 502. In an "on" state, hot melt adhesive is directed along flow paths defined by the supply passage 516, adhesive distribution channel 518, vertical passages 530, and adhesive passages 536 formed in the nozzle inserts 534. The hot melt adhesive is emitted through material outlets 540 (FIG. 14) of the nozzle inserts 534 as strands 554a that are directed toward surface 548 of moving substrate 550.

At the same time that hot melt adhesive is emitted through the material outlets 540 in strand form, pressurized air is directed along flow paths defined by the air passages 520, air distribution channel 542, passages 544, and air passages 546 formed through the lower surface 528 of pattern die 502. The pressurized air is emitted through air outlets 556 (FIG. 14) positioned on opposite sides of each material outlet 540 as described in detail above. Die assembly 500 is operable to emit the strands 554a of hot melt adhesive that are drawn down and attenuated into fibers 554b for deposition on the surface 548 of the moving substrate 550 as described above with reference to the embodiment of the die assembly 20 of FIGS. 1–12. It will be appreciated by those skilled that the art that the nozzle inserts 534 and air passages 546 may be modified to incorporate the configurations shown and described above with reference to FIGS. 1–12. Moreover, it will be appreciated that while nozzle inserts 534 are preferred, they may be replaced with a series of adhesive passages drilled or otherwise formed in the lower surface 528 of the pattern die 506.

FIGS. 15, 15A and 16 illustrate a modular die assembly 600 in accordance with another alternative embodiment of the present invention. Die assembly 600 is mounted to a lower end of a dispenser body 602 and includes a die block 604 similar to the die block 22 described in detail above, a distribution plate 606, a pattern die 608, and a sealing plate 610. The distribution plate 606, pattern die 608 and sealing plate 610 are mounted within a seat 612 defined by a vertical wall or surface 614 and a horizontal wall or surface 616 formed in die block 604. It will be appreciated that the dispenser body 602 is similar in structure and operation to the dispenser body 18 described in detail above.

As best understood with reference to FIGS. 15 and 16, each of the distribution plate 606, pattern die 608 and sealing plate 610 includes a respective pair of apertures 618 extending through the die components for receiving a pair of fasteners 620 that mount the components to the vertical wall 614 of die block 604. Distribution plate 606 is mounted having a planar face 622 in engagement with the vertical wall or surface 614 of die block 604, and includes a pair of transverse air passages 624 extending through the plate 606 that fluidly connect with a respective pair of air passages 626 (one shown in FIG. 16) formed in die block 604. Distribution plate 606 further includes a transverse adhesive passage 628 extending through the plate 606 that fluidly connects with an adhesive supply passage 630 formed in die block 604 (FIG. 16). For purposes to be described in greater detail below, a pair of vertically oriented air distribution channels 632a, and an elongated, horizontally oriented air distribution channel 632b, are formed in an opposite face 634 of distribution plate 606.

Pattern die 608 is mounted having a planar face 636 in engagement with the opposite face 634 of the distribution plate 606. As will be described in greater detail below, pattern die 608 includes respective upper and lower pairs of transverse air passages 638a and 638b that extend through the pattern die 608, with the upper pair of air passages 638a fluidly connected to the pair of air passages 624 in distribution plate 606, and each of the lower pair of air passages 638b fluidly connected to a respective one of the pair of vertically oriented air distribution channels 632a formed in the face 634 of die block 606. Pattern die 608 further includes an elongated, horizontally oriented adhesive distribution channel 640 formed in face 636 that fluidly connects with the transverse adhesive passage 628 formed in distribution plate 606.

As shown in FIGS. 15A and 16, pattern die 608 preferably includes six (6) adhesive passages 642, drilled or otherwise formed, that extend from a lower end 644 of the pattern die 608 and fluidly connect with the elongated, horizontally oriented adhesive passage 640 formed in pattern die 608. Each adhesive passage 642 terminates in a material outlet 646 at the lower end 644 of the pattern die 608. The material outlets 646 are preferably aligned along a common axis and are equidistantly spaced at the lower end 644 of the pattern die 608. Of course, it will be appreciated that the adhesive passages 642 may be replaced with tubular nozzle inserts (not shown), as described in detail above, without departing from the spirit and scope of the present invention. Air outlets 648 are formed between each material outlet 646 by respective angularly-shaped, upper and lower cutouts 650a and 650b formed on the lower end 644 and on opposite faces 636 and 652 of the pattern die 608 for purposes to be described in detail below.

As shown in FIGS. 15 and 16, the sealing plate 610 includes a pair of elongated, vertically oriented air distribution channels 654a and an elongated, horizontally oriented air distribution channel 654b formed in plate face 656 that engages face 652 of pattern die 608. Each of the vertically oriented air distribution channels 654a fluidly connects with an upper and lower air passage 638a, 638b of each respective pair of air passages 638a, 638b formed in the pattern die 608. As shown phantom in FIG. 16, the upper cutouts 650a on one side of pattern die 608 fluidly connect with the horizontally oriented air distribution channel 654b of sealing plate 610, while the upper cutouts 650a on the other side of pattern die 608 fluidly connect with the horizontally oriented air distribution channel 632b of distribution plate 606.

In operation, the die assembly 600 is mounted above a surface of a moving substrate (not shown) with its longitudinal axis preferably positioned generally transverse to the direction of travel of the moving substrate (not shown). In an "on" state of dispenser body 602, hot melt adhesive is directed along flow paths defined by the supply passage 630, adhesive passage 628, adhesive distribution channel 640, and vertically oriented adhesive passages 642. The hot melt adhesive is emitted through the material outlets 646 as strands (not shown) that are directed toward the surface of moving substrate (not shown), similar to strands 27a described in detail above.

At the same time that hot melt adhesive is emitted through the material outlets 646 in strand form, pressurized air is directed along flow paths defined by the air passages 626, air passages 624, upper air passages 638a, vertically oriented air distribution channels 654a, horizontally oriented air distribution channel 654b, lower air passages 638b, vertically oriented air distribution channels 632a, and horizontally oriented air distribution channel 632b.

As described above, the horizontally oriented air distribution channel 654a of distribution plate 606 fluidly connects with upper cutouts 650a on one side of pattern die 608, while the horizontally oriented air distribution channel 654b of sealing plate 610 fluidly connects with upper cutouts 650a on the opposite side of pattern die 608. In this way, pressurized air is emitted through the air outlets 648 formed between each of the material outlets 646. The air outlets 648 and material outlets 646 function substantially as described in detail above to draw down and attenuate each strand (not shown) of hot melt adhesive as it emits from a material outlet 646.

Figure 17:
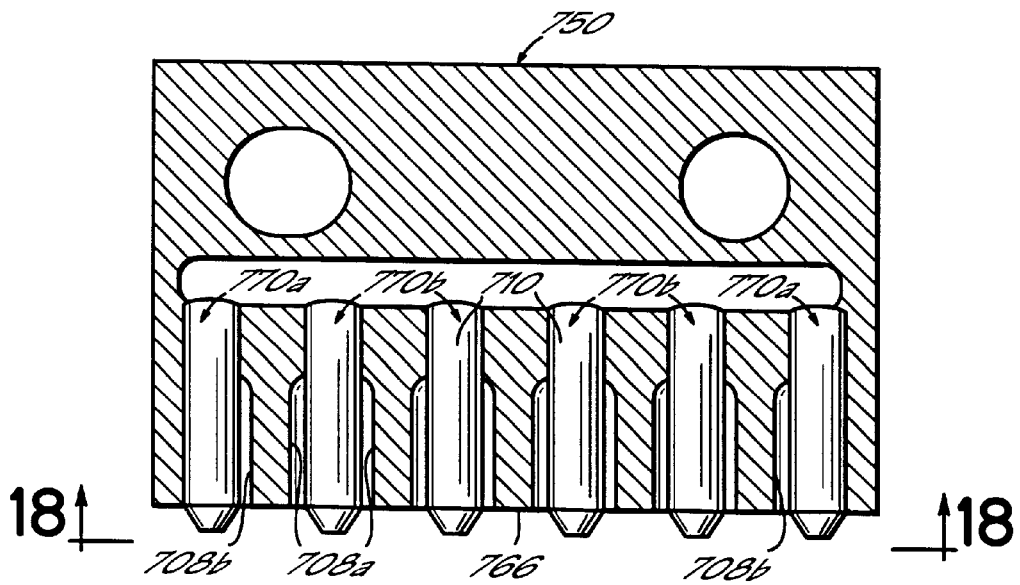
FIG. 17 is a view similar to FIG. 3, illustrating a pattern die in accordance with a sixth embodiment of the present invention.
Figure 18:
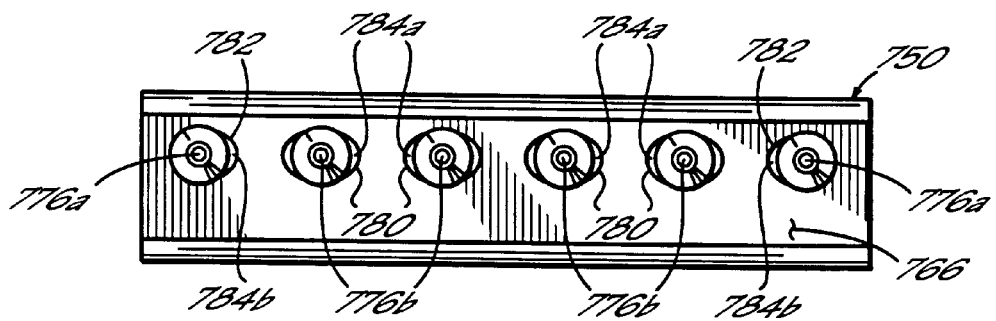
FIG. 18 is a bottom view of the pattern die illustrated in FIG. 17, taken along line 18—18 in FIG. 17.

In yet another embodiment of the present invention, as best understood with reference to FIGS. 17 and 18, a modified pattern die 750 is shown. All other components of the die assembly 20 are generally unchanged. In this embodiment, pattern die 750 preferably includes six (6) bores 764 formed through the lower surface 766 of the pattern die that extend upwardly and fluidly connect with the six (6) transverse passages (one shown in FIG. 2) extending horizontally inwardly from the adhesive distribution channel 62. The bores 764 are equidistantly spaced along the lower surface 766 and have a circular cross-section. The bores 764 are also preferably aligned along an axis that is generally parallel to the longitudinal axis of the pattern die. The bores 764 are sized to receive respective tubular inserts 770a and 770b that are inserted and frictionally engaged within the bores 764. The tubular inserts 770a define a pair of outer liquid material outlets 776a, while the tubular inserts 770b define inner liquid material outlets 776b. Four (4) oblong bores 780 and two (2) crescent bores 782 are formed through the lower surface 766 of the pattern die 150 that extend upwardly and fluidly connect with ten (10) transverse passages (not shown) extending horizontally inwardly from the horizontally oriented air distribution channel 60b. The ten (10) transverse passages (not shown) are similar to the twelve (12) transverse passages 82 described in detail above in connection with FIG. 2. The oblong bores 780 are equidistantly spaced, and are preferably aligned with their respective longitudinal axes aligned along an axis that is also generally parallel to the longitudinal axis of the pattern die 750 and coincident with the axis of bores 764. In this way, crescent-shaped air outlets 784a are formed on opposite sides of each material outlet 776a by a wall 708a of the oblong bores 780 and an outer cylindrical surface 710 of the tubular inserts 770a. Additionally, crescent-shaped air outlets 784b are formed axially inwardly of each material outlet 776b by a wall 708b of the crescent bores 782 and the outer cylindrical surface 710 of the tubular inserts 770b. The air outlets 784a, 784b and material outlets 776a, 776b function substantially as described in detail above to draw down and attenuate each strand 27a of hot melt adhesive as it emits from a material outlet 776a, 776b. By eliminating air outlets axially outwardly of each outer material outlet 776a, "necking" of the dispensed pattern, i.e., a reduction in the overall width of the dispersed pattern in the cross-machine direction, is reduced.

It will be appreciated by those skilled in the art that the material dispensing system 2 of the present invention provides improved control of dispensed material patterns on a moving substrate. The decreased volume of air required to produce a uniform layer of material on the substrate reduces the formation of undesirable "fly", and also reduces operational and maintenance costs of the material dispensing system 2. Additionally, the ability to increase the spacing between adjacent material outlets 76 per dispensing module 16 to form a uniform layer on the substrate (or to reduce the number of material outlets 76 per dispensing module 16) reduces the formation of undesirable "shot" during the critical draw down phase. The orientation of the dispensed pattern in narrow beams reduces the dispensed pattern footprint for improved pattern control. Moreover, the orientation and operation of the material outlets 76 and air outlets 84 improves the ability to modularize the dispensing system.

While the present invention has been illustrated by a description of various embodiments and while these embodiments have been described in considerable detail, it will be appreciated by those of ordinary skill in the art that departures may be made from such details without departing from the spirit or scope of applicants' invention. For example, while the terms "upper", "lower", "above" and "below" have been used herein to discuss one embodiment of the present invention, it will be understood that other orientations of the die components and substrate are possible without departing from the spirit and scope of the present invention. The invention in its broader aspects is therefore not limited to the specific details, representative apparatus and method, and illustrative example shown and described.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicants' general inventive concept.

Having described the invention, what is claimed is:

1. A pattern die for use in a system to dispense liquid material onto a moving substrate, comprising:

a pair of outer liquid material outlets and a plurality of inner liquid material outlets therebetween spaced along a common axis at one end thereof for dispensing a plurality of strands of liquid material toward the substrate, a pair of air outlets associated with each of said inner liquid material outlets, and a single air outlet associated with each of said outer liquid material outlets for emitting pressurized air operable to oscillate the dispensed strands in directions predominantly parallel with the common axis during flight toward the substrate and forming an overlapping pattern of liquid material on the moving substrate.

2. The pattern die of claim 1 further comprising a first plurality of elongated bores spaced along the common axis, and a second plurality of elongated bores in registry with and intersecting said first plurality of elongated bores.

3. The pattern die of claim 2 further comprising a plurality of tubular nozzle inserts received in said first plurality of elongated bores that each defines a respective one of said inner and outer liquid material outlets.

4. The pattern die of claim 3, wherein said second plurality of elongated bores defines, in combination with a wall of a respective one of said tubular nozzle inserts, a respective pair of said air outlets associated with each of said inner liquid material outlets.

5. The pattern die of claim 3, wherein said second plurality of elongated bores defines, in combination with a wall of a respective one of said tubular nozzle inserts, a respective one of said single air outlets associated with each of said outer liquid material outlets.

* * * * *